United States Patent
Noera et al.

(10) Patent No.: US 8,318,673 B2
(45) Date of Patent: Nov. 27, 2012

(54) ANTI-HEMORRHAGE MEDICATION PACK

(75) Inventors: Giorgio Noera, Modena (IT); Alfio Bertolini, Roncolo di Quattro Castella (IT)

(73) Assignee: Health Ricerca e Sviluppo S.R.L., Bologna (IT)

( * ) Notice: Subject to any disclaimer, the term of this patent is extended or adjusted under 35 U.S.C. 154(b) by 591 days.

(21) Appl. No.: 12/373,174

(22) PCT Filed: Jul. 6, 2007

(86) PCT No.: PCT/IB2007/052661
§ 371 (c)(1),
(2), (4) Date: Aug. 25, 2009

(87) PCT Pub. No.: WO2008/007322
PCT Pub. Date: Jan. 17, 2008

(65) Prior Publication Data
US 2009/0318361 A1 Dec. 24, 2009

(30) Foreign Application Priority Data
Jul. 10, 2006 (IT) .............................. MO2006A0222

(51) Int. Cl.
*A61K 38/35* (2006.01)
*A61M 5/20* (2006.01)

(52) U.S. Cl. ......... 514/9.7; 514/13.5; 514/15.6; 604/70; 604/84; 604/95.02; 604/144; 604/506; 604/522

(58) Field of Classification Search .................. None
See application file for complete search history.

(56) References Cited

U.S. PATENT DOCUMENTS

| | | |
|---|---|---|
| 5,380,710 A | 1/1995 | Bertolini |
| 6,406,455 B1 | 6/2002 | Willis et al. |
| 7,959,600 B2 * | 6/2011 | Chang et al. .................. 604/89 |
| 2003/0036725 A1 | 2/2003 | Lavi et al. |
| 2003/0125528 A1 * | 7/2003 | Hay et al. ..................... 530/409 |

FOREIGN PATENT DOCUMENTS

| | | |
|---|---|---|
| GB | 2388033 A | 11/2003 |
| WO | 00/29050 | 5/2000 |

OTHER PUBLICATIONS

Kirwan et al. The Effect of Therapeutic Glucocorticoids on the Adrenal Response . . . Arthritis & Rheumatism. May 2006, vol. 54, No. 5, pp. 1415-1421.*

* cited by examiner

*Primary Examiner* — Jeffrey E Russel
(74) *Attorney, Agent, or Firm* — Tutunjian & Bitetto, P.C.

(57) ABSTRACT

An anti-hemorrhage medication pack for administering an anti-hemorrhage drug, in particular for the treatment of hemorrhage caused by trauma in emergency situations comprises an active ingredient selected from the group comprising the 1-24 amino acid sequence of the adrenocorticotropic hormone (ACTH 1-24) and all its fragments and analogues, and analogues of fragments, with agonist activity on the MC4 melanocortin receptors, and all the synthesis agonists, including those with a nonpeptidic structure, of the MC4 melanocortin receptors. An auto-injector (1; 11) includes the drug for automatically injecting a patient with the drug.

9 Claims, 2 Drawing Sheets

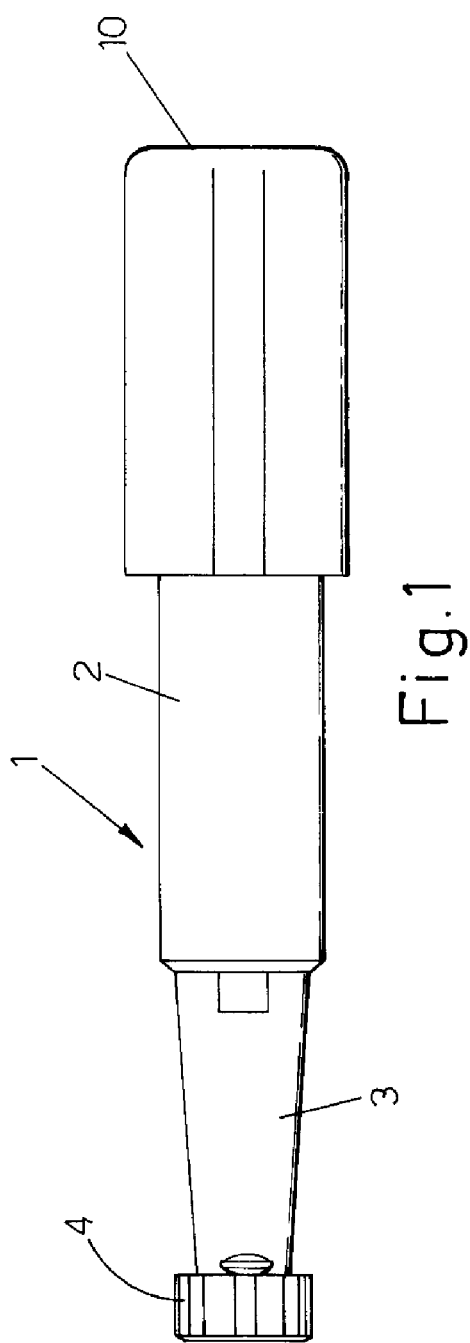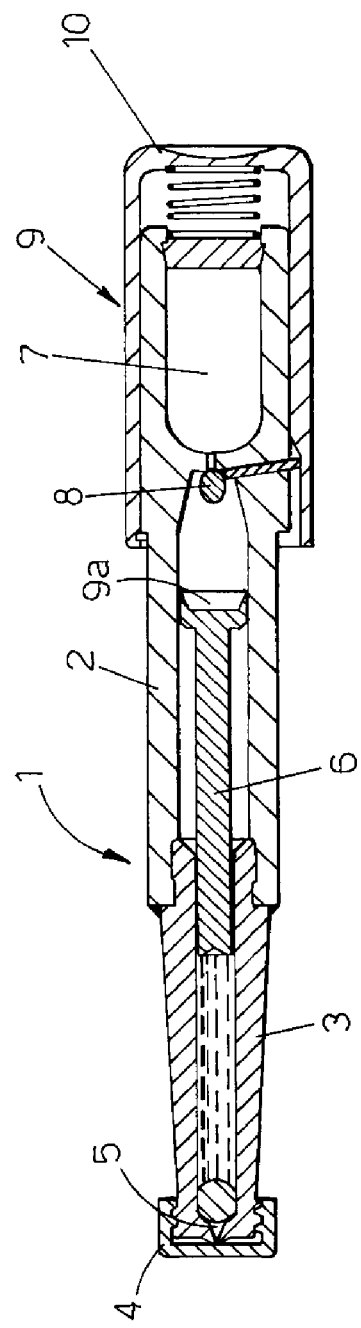

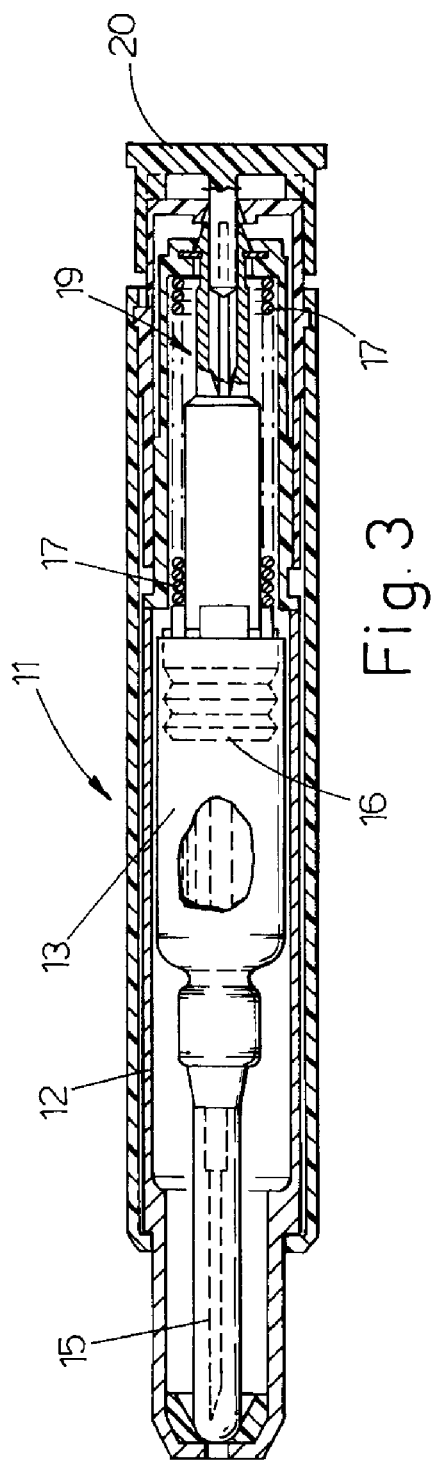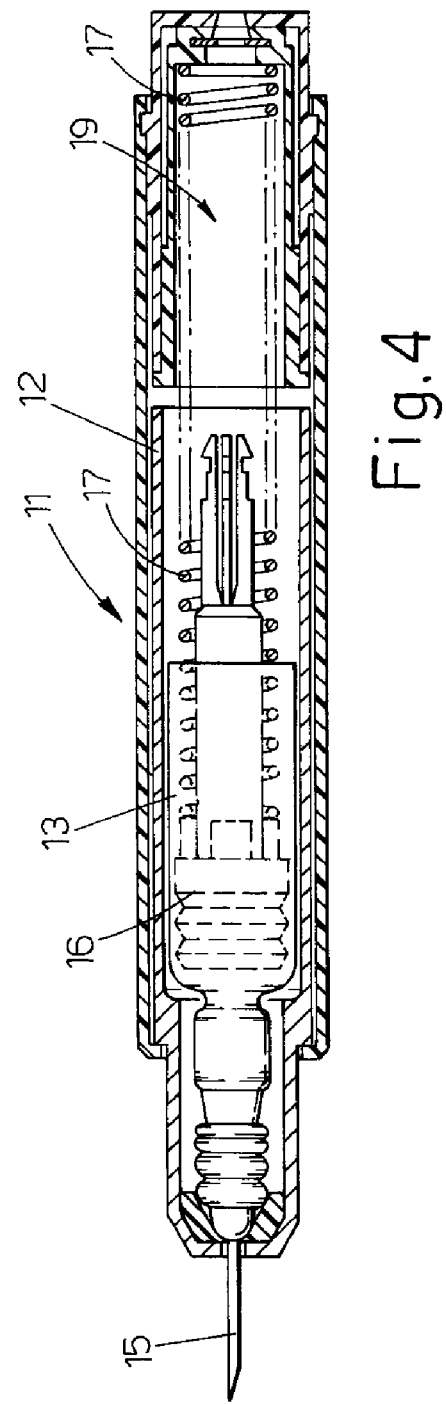

ANTI-HEMORRHAGE MEDICATION PACK

The invention concerns an anti-hemorrhage medication pack for the administration of an anti-hemorrhage drug, in particular for the initial treatment of hemorrhages in cases of trauma or critical events, for example in cases of road accidents or persons injured in war operations.

Critical Mass Events (CME) are catastrophic occurrences in which the territorial organisation for medical emergencies (OME) is unable to deal with the situation that has occurred.

All the resources necessary in the field are put into play in a manner directly proportional to the severity and extent of the event.

Two strategies are employed in the treatment of a patient injured in a Critical Mass Event or a trauma accident, differing mainly in their dynamics: the first strategy is characterised by mobility of the patient towards a hospital structure, defined also with the term "Scoop and Run"—literally scoop up (the patient's body) and run (towards the hospital), abbreviated hereinafter with SaR—while the second strategy uses the mobility of the medical-health professional towards the patient, defined with the term "Stay and Play", stay in place and work at the scene, thus delaying the movement of the patient in order to increase his/her stability for the subsequent journey towards the hospital.

In emergency medicine, the term "Golden Hour" is used to define the 60-minute period that follows a traumatic event or a serious disease. The patient's, possibilities of survival are greater if medical intervention takes place within the "Golden Hour". The "Scoop and Run" and "Stay and Play" strategies also differ in terms of cost and the type of medical personnel training required.

In the case of Critical Mass Events, both strategies involve planning of patient transport towards a hospital: from the fast "Scoop and Run" (SaR), to initial medical treatment of the patient on the scene with the "Stay and Play" strategy.

Both strategies have advantages and disadvantages, and a combination of these two opposing strategies has led to the conception of a new strategy defined as "Play and Run".

The time that cannot be reduced—for example, the time necessary to extract the victim of a road accident from a car—is used to carry out initial medical care.

For example, with the "Play and Run" strategy, the objective of the medical treatment is no longer to restore normal blood pressure but to achieve minimum blood pressure, using not just intravenous infusion but also vasoconstrictors or antishock trousers to compress the legs and force the blood into the rest of the body.

The aim is to reduce the risk of death due to the trauma of the transport while trying to respect the "Golden Hour" rule, that is to say the transport of the patient to a hospital within one hour of the traumatic event.

The "Scoop and Run" (SaR) strategy is an obligatory choice, in view of its demonstrated efficacy, for requirements linked to risk factors, limited transport times and the type of injury.

For example, in war operations under enemy fire, the patient may suffer penetrating wounds which require immediate transfer to a hospital or Trauma Centre, that is to say a hospital structure dedicated to the treatment of patients with serious trauma injuries.

To achieve this objective, evacuation times must be extremely limited, even resorting when possible to the ability to concentrate personnel means and materials, staying within the "Golden Hour".

SaR is currently the strategy most commonly used by all forces operating in war situations and has largely replaced specialised care on the spot also because of the possibility that some injuries cannot be detected there and then and can become critical while the injured patient is still far away from the hospital.

However, even the most speeded up rescue and the increased skills in medical assistance are not sufficient to guarantee the survival of a patient in cases of severe penetrating wounds.

In fact, the most frequent injuries encountered in war zones are those caused by bullets, splinters, explosions and in general by all the injuries that in war jargon are defined by the term "blast", often accompanied by abundant hemorrhage.

According to recent studies, the hemorrhagic shock caused by this type of injury, even if the wound has been promptly plugged, rapidly becomes irreversible and leads to death in up to 40% of patients.

Recent and distressing episodes in zones outside the areas of high operational intensity have highlighted the need to study this problem in greater depth in order to find a useful life-saving means to reduce the incidence of death following "blast" injuries.

The percentage of mortality of a critical patient in hemorrhagic shock is directly proportional to time (1 hour: 10%; more than 10 hours: 75%), if appropriate aid is not given.

The two critical factors are the stabilization of the patient by reanimation at the scene of the incident and transfer to a suitably equipped and organised unit behind the lines.

The degree of efficacy and efficiency of the medical assistance are determined by the relationship between the various steps in the process and the time in which the number of the victims are handled and their management by the number of medical staff available and their competence, the availability and quality of the hospitals or trauma centres that can be used, and finally by the logistic organisational stages.

The usual medication packs known to prior art give a result whereby around 40% of patients suffering from "blast" injuries risk dying even if promptly cared for by trained personnel.

In fact, when the hemorrhage has already occurred, an inevitable chain of unfavourable hemodynamic events connected with the shock is triggered.

The individual's biological response which contrasts with the degree of the injury received is defined as the "survival constant". The interruption of this contrast is the threshold limit at which the victim enters into shock as the sole premortal response.

The state of shock is characterised by a cascade of biochemical events that take place up to the level of non-reversibility. The point of no return appears before the death of the subject and cannot be treated.

Rapid intervention increases the percentages of success, although it is not known when and how irreversibility begins. In the aid process, this point has absolute priority and absorbs most management resources.

The cardiovascular failure that occurs when a person is in shock is also due to a massive release of endogenous opioids which act through venodilation, that is to say with a stagnation of venous blood which does not therefore reach the heart, and also through a depression both in the tone of the sympathetic nervous system and of the release of noradrenaline by the nerve ends. This contributes to precipitation of an impairment of the microcirculation with stagnation of the arterial blood also in the capillaries and triggers a non-bacterial generalised inflammatory reaction with the activation of various cells, and the release of various chemical substances including, as the result of enzymatic activation, the particularly significant hyperproduction of nitrous oxide (NO).

This excess production of nitrous oxide (NO) is also responsible for the low arteriole responsivity to vasoconstrictors and for the inhibited release of noradrenaline by the nerve ends.

It is therefore necessary to mobilise the remaining residual blood, unutilised in these circumstances as it is stagnated, as soon as possible. This necessity is a priority in the operating theatre just as it is in war injuries, critical mass events, etc.

One aim of the invention is to improve the known types of anti-hemorrhage medication packs.

Another aim of the invention is to present an anti-hemorrhage medication pack that is simple to use even by non-specialised personnel.

Yet another aim is to present an anti-hemorrhage medication pack that is economical to produce.

According to one aspect of the invention, an anti-hemorrhage medication pack as specified in claim 1 is presented.

Thanks to the auto-injector form of application, the anti-hemorrhage medication pack according to the invention can also be used by non-medical or non-nursing personnel.

Furthermore, the use of an active ingredient based on the adrenocorticotropic hormone (ACTH) makes it possible to stabilise the patient in shock for a period of at least 3 hours and thus to delay the reversibility of the shock for at least 2 hours.

BRIEF DESCRIPTION OF THE DRAWINGS

The invention can be better understood and implemented by referring to the accompanying drawings, which illustrate a non-binding example, in which:

FIG. 1 is a side view of a main component of the anti-hemorrhage medication pack according to the invention;

FIG. 2 is a cross-section of the main component in FIG. 1;

FIG. 3 is a cross-section of another version of a component of the anti-hemorrhage medication pack according to the invention; and FIG. 4 is a cross-section of the component in FIG. 3 after performing an injection.

The medication pack according to the invention is contained in a package (not shown), which includes an auto-injector filled with an antishock drug and a leaflet (not shown) with written instructions on how to administer the antishock drug.

According to what is shown in FIGS. 1 and 2, a first version of the auto-injector 1 has no needle and comprises a main body 2, a container 3 containing an antishock drug in liquid form, a cap 4 which closes a nozzle 5 connected to the container 3.

The nozzle 5 must be positioned in direct contact with the patient's skin and thanks to the high speed at which the drug passes through the nozzle 5, the drug in the container 3 passes through the patient's skin.

The drug is therefore injected into the patient's body even without a needle.

The container 3 is equipped with a piston 6 driven by actuator means 9 comprising pneumatic means that are equipped with a chamber 7 containing an inert pressurised gas.

By breaking a dividing membrane 8, the chamber 7 with the pressurised gas comes into communication with an actuator 9a connected to the piston 6. The piston 6 is then activated at high speed by the gas in the chamber 7 and the drug is consequently passed through the nozzle 5 at high speed.

FIGS. 3 and 4 show the version of an auto-injector 11 equipped with a needle 15. The auto-injector 11 comprises an outer casing 12 that can house the needle 15 in a retracted position, a container 13 connected to the needle 15 and containing an antishock drug; the auto-injector 11 also comprises actuator means 19 to perform the injection.

The actuator means 19 comprise elastic means 17 which first cause the needle 15 to move forward, and then carry out the injection of the antishock drug by activating a piston 16 which moves inside the container 13.

In FIG. 3 the auto-injector 11 is ready to carry out an injection with the antishock drug inside the container 13. FIG. 4 shows the auto-injector 11 in a condition in which the injection has been carried out, with the needle 15 extracted and the container 13 emptied.

In another version of the invention (not shown) which can be used both with an auto-injector with a needle and with an auto-injector without a needle, the pharmacological part is freeze-dried and a long storage time (around 60 months) is therefore possible.

In this version, the freeze-dried pharmacological part is in a first container separate from the second container which holds the liquid part of the drug.

When the auto-injector is used, the actuator means 9, 19 connect the first and second containers, for example by breaking a dividing wall, and mix the freeze-dried part of the drug with the liquid part.

The antishock drug is thus formed only at the time of use and can be stored for long periods even in adverse climatic conditions, for example at high temperatures.

When used, both types of auto-injector 1, 11 must be placed directly in contact with the patient's skin and held there with moderate pressure until the injection has been carried out. To activate the auto-injectors 1, 11 it may be necessary to remove a safety element and then activate a control 10, 20.

According to the invention, the active ingredient of the antishock drug used in the auto-injectors 1, 11 contains a polypeptide selected from a group comprising the 1-24 amino acid sequence of the adrenocorticotropin hormone (ACTH 1-24) and all its fragments and analogues, and analogues of fragments, with agonist activity on the MC4 melanocortin receptors, that is to say a polypeptide that binds to MC4 melanocortin receptors with consequent biochemical and/or physiological responses, and all the synthesis agonists, including those with a non-peptidic structure, of the MC4 melanocortin receptors. In particular, the active ingredient can be tetracosactide hexacetate. It should be pointed out that the antishock effects of melanocortin peptides are not mediated by the adrenal glands (corticosteroids) as these effects are obtained experimentally both with melanocortin preparations without corticotrophin activity and in adrenalectomised animals.

The antishock effect of melanocortins, peptides which bind to specific receptors in the central nervous system, MC4 receptors, takes place by restoring the vasomotor reflex rendered inactive by the sequestration of peripheral blood due to the massive release of noradrenaline and the activation of the inflammatory cascade ending in enzymatic activation and production of nitrous oxide, following the secretion of opioids from stage two to the irreversible stage of shock.

This restoring takes place precisely because of the action opposing the opiods and the nitrous oxide.

The melanocortins free the blood previously taken away from the circulation because of stagnation, making this quantity of blood available once again.

The blood brought back into circulation in this way is particularly precious since it is used as if it were a reserve of blood in the patient's body which has lost blood because of the hemorrhage.

The shock reversibility curve can thus be moved by using one of the above-mentioned antishock drugs, for example tetracosactide hexacetate, as, with a single, effective and low-cost treatment, it is able to counter the time factor in the out-of-hospital aid process, intervening significantly in all the critical points indicated above.

For a single treatment of shock the drug dose of 10 mg makes it possible to stabilise the patient in shock for a period of at least 3 hours and thus to shift the shock reversibility for at least 2 hours.

The patient can therefore lose up to 50-60% of the circulating blood mass in this period, considerably increasing the incidence of survival up to 90%.

The drug indicated above is injected intramuscularly or intravenously (intralingual, intraosseous) by means of the auto-injector 1, 11, and its action takes place in 5 to 15 minutes.

The drug according to the invention is not toxic and can be administered without side effects even to healthy persons; thanks to the form of application with an auto-injector it can also be used by non-medical or non-nursing personnel.

The drug according to the invention can replace the infusion therapy of 1-3 litres of liquids or blood that is normally used in these cases.

The advantages with respect to medical aids currently used in the event of hemorrhage are:
- low production cost and high clinical efficacy in all types of shock;
- lower cost with respect to blood, its preservation and supplying;
- lower cost with respect to a volume expander;
- low transport cost and logistic availability;
- medical skills not necessary;
- possibility of using an auto-injector;
- in the version with a freeze-dried pharmacological part, it is possible to store the medication pack for a long period of time, for example up to 60 months.

The invention claimed is:

1. An anti-hemorrhage medication pack for administering an anti-hemorrhage drug for the treatment of a hemorrhage caused by trauma comprising:
   a drug with an active ingredient selected from the group consisting of a 1-24 amino acid sequence of adrenocorticotropic hormone (ACTH 1-24) and all its fragments and analogues, and analogues of fragments, with agonist activity on MC4 melanocortin receptors, and synthetic agonists of the MC4 melanocortin receptors; and
   an auto-injector including the drug for automatically injecting said drug into a patient, said auto-injector including
   a first container suitable for containing a lyophilized pharmacological part of the anti-hemorrhage drug and a second container for containing a liquid part of the anti-hemorrhage drug;
   actuating means configured for
      connecting the first and second container, by interrupting a dividing wall, thereby mixing the lyophilized pharmacological part with the liquid part of the anti-hemorrhage drug only at the moment of
      administering the injection to the patient, and automatically injecting said mixed anti-hemorrhage drug into the patient.

2. A pack according to claim 1, wherein the auto-injector has no needle.

3. A pack according to claim 1, wherein the auto-injector is equipped with a needle.

4. A pack according to claim 3, wherein the needle is normally in a retracted position and is in an extracted position when an injection is carried out.

5. A pack according to claim 1, wherein said actuating means extracts a needle wherein the needle is normally in a retracted position and is in an extracted position when an injection is carried out.

6. A pack according to claim 1, wherein said actuating means comprises pneumatic means.

7. A pack according to claim 1, wherein said drug comprises tetracosactide hexacetate.

8. A package comprising a pack according to claim 1 and a leaflet with written instructions for administration of the drug.

9. An anti-hemorrhage medication pack for administering an anti-hemorrhage drug for the treatment of a hemorrhage caused by trauma comprising:
   a drug with an active ingredient selected from the group consisting of a 1-24 amino acid sequence of adrenocorticotropic hormone (ACTH 1-24) and all its fragments and analogues, and analogues of fragments, with agonist activity on MC4 melanocortin receptors, and synthetic agonists of the MC4 melanocortin receptors; and
   an auto-injector including the drug for automatically injecting said drug into a patient, said auto-injector including
   a first container suitable for containing a lyophilized pharmacological part of the anti-hemorrhage drug and a second container for containing a liquid part of the anti-hemorrhage drug;
   actuating means comprising pneumatic means configured for
      connecting the first and second container by breaking a dividing wall, thereby mixing the lyophilized pharmacological part with the liquid part of the anti-hemorrhage drug only at the moment of administering the injection to the patient, and
      automatically injecting said mixed anti-hemorrhage drug into the patient.

* * * * *